United States Patent [19]

Nigay

[11] Patent Number: 5,004,463
[45] Date of Patent: Apr. 2, 1991

[54] PERMANENT RECEPTACLE FOR COLLECTING URINE FROM WOMEN

[75] Inventor: Pierre Nigay, Compiegne, France

[73] Assignee: Kilrush Limited, London, United Kingdom

[21] Appl. No.: 477,913

[22] PCT Filed: Oct. 28, 1988

[86] PCT No.: PCT/FR88/00530
§ 371 Date: Apr. 30, 1990
§ 102(e) Date: Apr. 30, 1990

[87] PCT Pub. No.: WO89/04156
PCT Pub. Date: May 18, 1989

[30] Foreign Application Priority Data

Oct. 30, 1987 [FR] France .................... 87 15093

[51] Int. Cl.⁵ .................... A61F 5/44; A61B 5/00; A47K 11/00
[52] U.S. Cl. .................... 604/329; 128/761; 4/144.3; 604/327; 604/331
[58] Field of Search ............... 128/761; 604/327, 329, 604/330, 331; 4/144.1, 144.3, 144.4

[56] References Cited

U.S. PATENT DOCUMENTS

| 3,194,238 | 7/1965 | Beece, Jr. | 604/329 |
| 3,703,731 | 11/1972 | Leiser | 4/144.3 |
| 4,198,979 | 4/1980 | Cooney et al. | 604/331 |
| 4,583,983 | 4/1986 | Einhorn et al. | |
| 4,631,061 | 12/1986 | Martin | 128/761 |
| 4,936,838 | 6/1990 | Cross et al. | 128/761 |

FOREIGN PATENT DOCUMENTS

| 2624004 | 6/1989 | France | 604/329 |
| 2126902 | 4/1984 | United Kingdom | 604/330 |
| 2129686 | 5/1984 | United Kingdom | 604/329 |

Primary Examiner—Robert Frinks
Assistant Examiner—Robert Clarke
Attorney, Agent, or Firm—Darby & Darby

[57] ABSTRACT

A permanent receptacle for collecting urine from women comprises a tray (2) and an oblong bevelled funnel (5) which co-operates with the urethra; the tray has a raised lip (4) conformed to surround the female organs, inside which is located said funnel (5) surround by a gutter (10) and, on one side only by a basin (12); the funnel (5) and the gutter (10) communicate with a collecting enclosure adjacent to the tray. The collecting enclosure has emptying means associated with a pumping system.

3 Claims, 1 Drawing Sheet

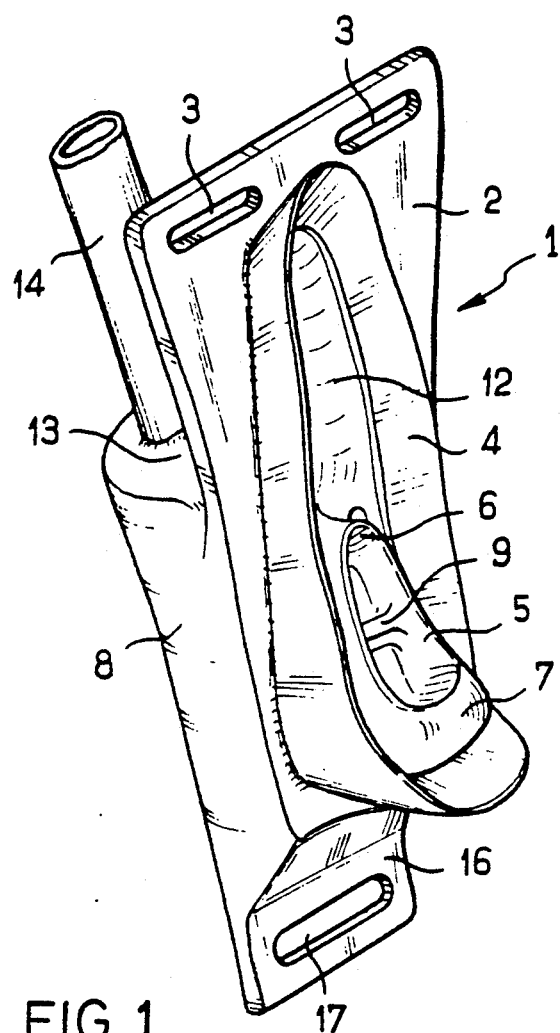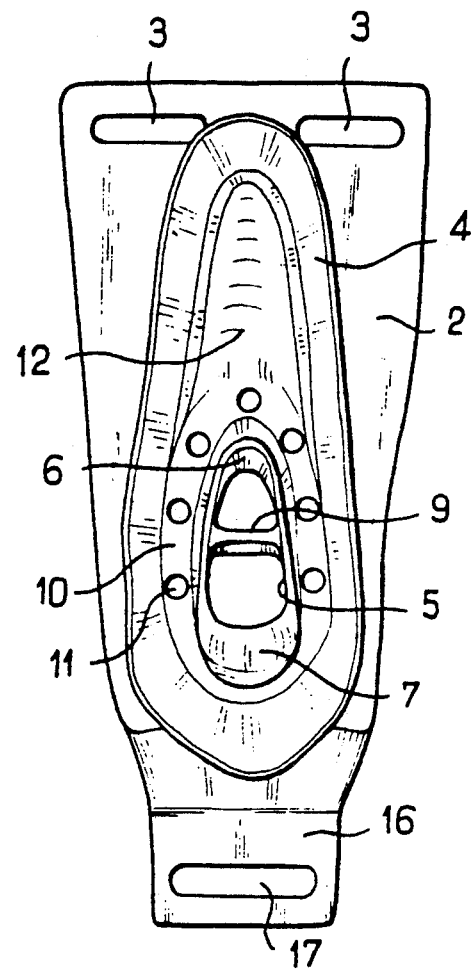
FIG.1
FIG.2
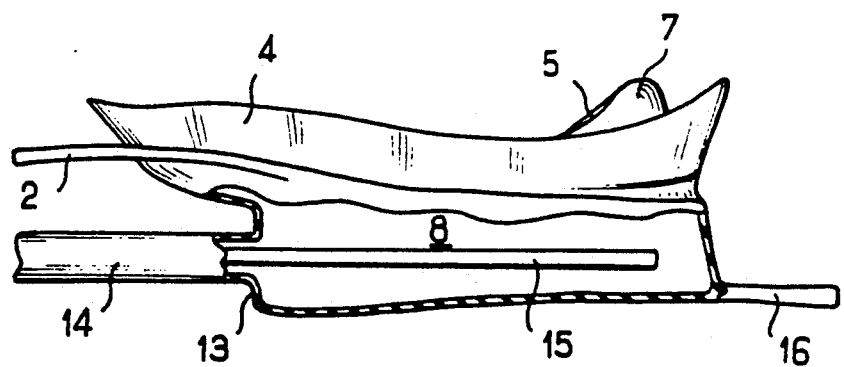
FIG.3

PERMANENT RECEPTACLE FOR COLLECTING URINE FROM WOMEN

The invention relates to a permanent urine-collecting receptacle for women.

European patent document No. A-148 047 and European patent document No. A-287 441 disclose equipment intended for the incontinent and making it possible to detect and pump the urine collected in the urinary tract in order to store it in a flexible bag, which is generally held by a belt.

This equipment is satisfactory but, in some cases, collection of the urine is less than perfect, especially when the subject adopts certain positions, in particular a lying position. Furthermore, in cases of both urinary and fecal incontinence, the operation of this equipment is found to be upset by the discharge of feces.

Female incontinence is more widespread than male incontinence and improved collecting receptacles for women have already been proposed.

Thus urine drainage devices are known which are worn permanently by the subject. U.S. Pat. Document No. A-4,583,983 shows such a drainage device, which has a plate and a beveled oblong duct for cooperating with the urethra at the urinary meatus in order to collect the urine, which is then discharged directly under gravity into a flexible bag. Although this drainage device can prove satisfactory in the simplest cases, i.e. when the female organs are of a regular shape and when the subject is in a vertical position, it is clear that it is not satisfactory when the subject is in a lying position and/or when the anatomy of the urinary region is disturbed, for example following the prolapse of an organ.

Temporary collecting receptacles of the urinal kind are also known. For example, European patent document No. A-185 517 shows such a urinal which is intended to be used exclusively on a temporary basis by a subject who is lying down. This is totally different from the permanent collecting receptacles to which the present invention relates.

The object of the invention is to prepare a permanent receptacle which is devoid of the above-mentioned disadvantages and which is particularly suitable for use with the detection and pumping equipment mentioned at the beginning of this specification.

The invention achieves its object by proposing a receptacle of the plate and duct type in which the plate has a raised lip shaped so as to surround the female organs, the said duct being located in the interior zone of the said lip and being surrounded by a channel and, on one side only, by a dish; the duct and the channel communicate with a collecting chamber adjoining the plate.

By virtue of a degree of flexibility, the raised lip ensures perfect leaktightness between the collection zone and the outside, in either direction. On the one hand, irrespective of the position of the female subject, the urine passed is collected either by the duct in the most normal case, or by the dish and the channel in other cases, with no leakage to the outside. On the other hand, the rear part of the lip forms a barrier to the discharge of any feces which might disturb the operation of the device.

The collecting chamber has discharge means which can be a gravity flow orifice connected, for example, to a receiving bag situated lower down; more advantageously, these means are associated with a detection and pumping system, for example the one in the patents cited at the beginning of this specification.

In that case, the discharge means are advantageously provided in the top part of the chamber.

The receptacle is preferably obtained by flow casting from a semi-flexible material such as a natural latex, whose flexibility makes it possible to avoid harshness on the female organs and to fit their contour more easily.

Further characteristics and advantages of the invention will become apparent from the following description of a preferred embodiment. Reference is made to the attached drawings, in which:

FIG. 1 is a ¾ perspective of the receptacle of the invention;

FIG. 2 is a top view of the same receptacle; and

FIG. 3 is a side view thereof with a partial cutaway.

The receptacle 1 is a semi-flexible semi-rigid article advantageously made of natural latex and obtained by molding.

It has a plate 2 in the shape of an inverted isosceles triangle, the upward-pointing base of which has two openings 3 for the passage of front suspension straps.

A relatively flexible sealing lip 4, whose closed contour is intended to surround the female organs, is situated on top of the plate 2. The lip 4 widens slightly outwards.

A hollow collecting duct 5, oblong in shape (in top view; cf. FIGS. 1 and 2) and beveled (in side view; cf. FIGS. 1 and 3), is provided inside this lip 4, in a lower offset position, the front part 6 of the said duct being lower than its rear part 7. The duct passes right through the plate 2 and communicates with an elongate collecting chamber 8 formed underneath the plate 2 and adjoining the latter.

Between its two substantially parallel edges, the duct 5 possesses an intermediate partition 9, preventing the said edges from closing together.

At the foot of the duct 5 and all around it, a channel 10 can collect and guide the liquid into the chamber 8 through orifices 11 provided in the bottom of the channel. The orifices 11 serve as vents when the chamber 8 is filled through the duct 5.

Towards the upper front part of the zone inside the lip 4, an elongate dish 12 can collect the liquid and direct it towards the channel 10.

Underneath the plate 2, the chamber 8 is provided, on an upper frontal wall 13, with a discharge tube 14 connected to the pumping system described in patents mentioned above. FIG. 3 shows the end of the suction pipe 15.

The shape of the chamber 8 and the position of the suction pipe 15 and of the detection electrodes are advantageously designed so as to retain a small permanent quantity of liquid in the bag, thereby avoiding noise phenomena associated with the presence of air in the pumping circuits.

At the bottom of the chamber 8, there is a lug 16 provided with a slit 17 for a lower fixing strap to pass through. If appropriate, this support lug 16 can be joined to a stool-retaining device next to the urine-collecting device.

What is claimed is:

1. A permanent urine-collecting receptacle for women, of the type having a plate and a bevelled oblong duct for cooperating with the urethra, characterized in that the plate has a raised flexible lip (4) shaped so as to surround the female organs, said duct (5) being located in the interior zone of said lip and being surrounded by a channel (10) and, on one said only, by a dish (12), and the duct (5) and the channel (10) communicating with a collecting chamber (8) adjoining the plate, said receptacle being formed from a semi-flexible material.

2. The receptacle according to claim 1, wherein the collecting chamber (8) has discharge means (14,15).

3. The receptacle according to claim 2, wherein the discharge means are associated with a pumping system.

* * * * *